United States Patent [19]

Chou et al.

[11] Patent Number: 5,256,798
[45] Date of Patent: Oct. 26, 1993

[54] PROCESS FOR PREPARING ALPHA-ANOMER ENRICHED 2-DEOXY-2,2-DIFLUORO-D-RIBOFURANOSYL SULFONATES

[75] Inventors: Ta-Sen Chou; Charles D. Jones, both of Indianapolis, Ind.

[73] Assignee: Eli Lilly and Company, Indianapolis, Ind.

[21] Appl. No.: 902,305

[22] Filed: Jun. 22, 1992

[51] Int. Cl.$^5$ .......................................... C07D 307/20
[52] U.S. Cl. ...................... 549/478; 549/476
[58] Field of Search ...................... 549/475, 476, 478

[56] References Cited

U.S. PATENT DOCUMENTS 4,526,988  7/1985  Hertel ............................... 549/313
4,965,374 10/1990  Chou et al. ........................ 549/313

OTHER PUBLICATIONS

Hoffer, et al., *Chem. Ber.*, 93, 2777–2781 (1960).
Capon, B., *Chemical Reviews*, 69 (4), 440–441, (1969).
Hubbard, et al., *Nucleic Acids*, 12, 6827 (1984).

*Primary Examiner*—C. Warren Ivy
*Assistant Examiner*—A. A. Owens
*Attorney, Agent, or Firm*—Sidney Persley; Leroy Whitaker

[57] ABSTRACT

A process for providing an alpha-anomer enriched ribofuranosyl sulfonate from a beta-anomer ribofuranosyl sulfonate; comprising treating a beta-anomer ribofuranosyl sulfonate or anomeric mixture thereof with a conjugate anion of a sulfonic acid source at elevated temperatures in an inert solvent.

22 Claims, No Drawings

PROCESS FOR PREPARING ALPHA-ANOMER ENRICHED 2-DEOXY-2,2-DIFLUORO-D-RIBOFURANOSYL SULFONATES

BACKGROUND OF THE INVENTION

1. Field of the Invention

The invention pertains to a process for preparing alpha-anomer enriched 2-deoxy-2,2-difluoro-D-ribofuranosyl sulfonates for use as intermediates in the preparation of known anti-tumor and anti-viral agents.

2. State of the Art

Stereoselective processes for preparing nucleosides involve stereochemical inversion of a furanose sugar at the anomeric position, therefore when β-nucleoside is the desired product, an appropriate sugar intermediate enriched in alpha anomer is preferably used as the substrate in the glycosylation reaction.

Capon, Brian, *Chemical Reviews*, 69 (4), 440-441 (1969) proposed a mechanism by which methyl ribofuranosides anomerize in methanol but made no mention of conditions under which one anomer might be obtained in preference to another.

Due to the instability of 2-deoxy-D-erythropentofuranosyl sulfonates, they are conspicuously absent from the chemical literature and therefore are rarely used in glycosylation reactions. The most frequently used 2-deoxyribofuranosyl derivative is 1-chloro-2-deoxy-3,5-(di-O-p-toluoyl)-α-D-erythro-pentofuranose which was first prepared by M. Hofer, *Chem. Ber.*, 93, 2777 (1960). This is because the compound is crystalline exists exclusively in the α configuration at C-1 position. However, the 2-deoxyribofuranosyl nucleosides prepared from the glycosylation of this α-chloro derivative with nucleobase are not obtained stereoselectively. Hubbard, et al., *Nucleic Acids*, 12, 6827 (1984) reported that this α-chloro derivative anomerizes in organic solvents at ambient temperature and forms the corresponding β-chloro derivative which was primarily responsible for the formation of α-nucleosides during glycosylation. Hubbard evaluated the anomerization in several solvents and found a solvent that held the anomerization to a minimum so that the desired β-nucleoside was obtained in high yield.

We have found that 1-halo and 1-methanesulfonate derivatives of 2-deoxy-2,2-difluororibofuranose are stable in certain organic solvents. For example, heating a solution of 2-deoxy-2,2-difluororibofuranosyl methanesulfonate of a known anomeric configuration at C-1 position in an inert organic solvent to 130° C. for extended periods of time does not affect the anomeric configuration of the anomer.

There is a need for an anomerization process that provides alpha-anomer enriched ribofuranosyl sulfonates from beta-anomer ribofuranosyl sulfonates.

Accordingly, one object of the present invention is to provide an anomerization process that provides alpha-anomer enriched ribofuranosyl sulfonates from beta-anomer ribofuranosyl derivatives.

Another object of the present invention is to provide an anomerization process that provides alpha-anomer enriched ribofuranosyl sulfonates in high yield.

Other objects and advantages of the present invention will become apparent from the following description of embodiments.

SUMMARY OF THE INVENTION

The invention is an anomerization process for providing an alpha-anomer enriched ribofuranosyl sulfonate of the formula

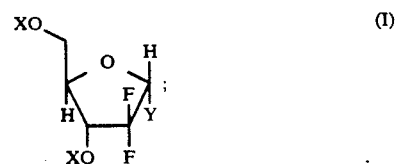

from a beta-anomer ribofuranosyl sulfonate of the formula

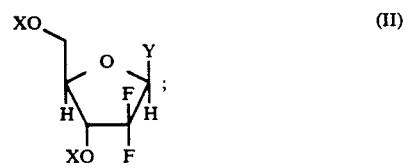

wherein Y is a sulfonate and each X is independently selected from hydroxy protecting groups; comprising treating a beta-anomer ribofuranosyl sulfonate of formula II with a source of a conjugate anion of a sulfonic acid, at elevated temperatures, in an inert solvent.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "xylenes" alone or in combination refers to all isomers of xylene and mixtures thereof. The term "lactol" alone or in combination refers to 2-deoxy-2,2-difluoro-D-ribofuranose. The term "sulfonate" alone or in combination refers to compounds of the general formula $BSO_3$; wherein B is an alkyl, substituted alkyl, aryl or substituted aryl group. The term "conjugate anion" refers to an anion of the general formula $BSO_3-$; wherein B is as defined above. The term "substituted" alone or in combination refers to the replacement of hydrogen or a common moiety by one or more of the groups selected from cyano, halo, carboalkoxy, aryl, nitro, alkoxy, alkyl, and dialkylamino. The term "anomerization" alone or in combination refers to epimerization at the C-1 postition of the ribofuranosyl derivative. The phrase "anomer enriched" alone or in combination refers to an anomeric mixture wherein the ratio of a specified anomer is greater than 1:1 and includes a substantially pure anomer. The terms "halo" or "halide" alone or in combination refer to fluoro, chloro, bromo, iodo, and their corresponding anionic form. The term "alkyl" alone or in combination refers to straight, cyclic and branched chain aliphatic hydrocarbon groups which preferably contain up to 7 carbon atoms such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons such as chloroethane, 1,2-dichloroethane, dichloroethane, trifluoromethane and the like. The term "alkoxy" alone or in combination refers to compounds of the general formula AO; wherein A is alkyl. The term "aryl" alone or in combination refers to carbocyclic or heterocyclic groups such as phenyl, naphthyl, thienyl and substituted derivatives thereof. The term "aromatic" alone or in combination refers to benzene like structures containing $(4\pi+2)$ delocalized electrons.

The ribofuranosyl sulfonate of formula I or anomeric mixtures thereof are readily synthesized by standard procedures commonly employed by those of ordinary skill in the art. For example, U.S. Pat. Nos. 4,526,988 and 4,965,374 teach the synthesis of an anomeric mixture of 3,5-di-O-tert-butyldimethylsilyl or 3,5-di-O-benzoyl derivatives of 2-deoxy-2,2-difluoro-D-ribofuranosyl sulfonate. Pending U.S. patent application Ser. No. 07/902,143, filed comtemporaneously herewith, teaches the synthesis of beta-anomer enriched 2-deoxy-2,2-difluoro-D-ribofuranosyl-3,5-di-O-benzoyl-1-arylsulfonates. In a preferred embodiment, 2-deoxy-2,2-difluoro-D-ribofuranosyl-3,5-di-O-benzoyl-1-alkylsulfonates are employed in the present process.

We have found that the beta-anomer sulfonates are more reactive toward a nucleophile than their alpha-anomer counterparts, and by reacting the beta-anomer sulfonate derivative with source of a conjugate anion of a sulfonic acid in organic solvent at elevated temperatures, the equilibrium mixture favors the less reactive alpha-anomer sulfonate.

The hydroxy protecting groups (X) of the ribofuranosyl sulfonates of formulas I and II are known in the art and are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxy-carbonyl, methoxyacetyl; carbonate derivatives such as phenoxycarbonyl, t-butoxccarbonyl ethoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxy-methyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkyl-silyl and 1,1,3,3,-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

The conjugate anion of a sulfonic acid may be derived from a number of sources known to one of ordinary skill in the art. These include:

(a) neutralizing an alkyl or aryl sulfonic acid such as 1-methanesulfonic acid, p-methylbenzene sulfonic acid, ethanesulfonic acid, p-toluenesulfonic acid, benzenesulfonic acid, p-bromobenzenesulfonic acid and camphorsulfonic acid with an alkali metal base such as sodium hydroxide, sodium hydride, potassium hydroxide, potassium t-butoxide, sodium methoxide and the like;

(b) neutralizing the alkyl or aryl sulfonic acids above with an amine base such as triethylamine, trimethylamine, N,N-dimethylbenzylamine or N-methylmorpholine or with an aromatic nitrogenous base such as pyridine. Examples of conjugate anions of sulfonic acids prepared by this method include triethylammonium methanesulfonate, trimethylammonium methanesulfonate, N,N-dimethylbenzylammonium methanesulfonate, pyridinium methanesulfonate, triethylammonium (p-bromobenzene)sulfonate, tetraethylammonium (p-bromobenzene)sufonate, tetraethylammonium(p-toluene)sulfonate, pyridinium(p-toluene)sulfonate and pyridinium-3-nitrobenzenesulfonate; more preferred is triethylammonium methanesulfonate; and (c) finally, the conjugate anion of a sulfonic acid may be generated in-situ by reacting 2-deoxy-2,2-difluoro-D-ribofuranose with a sulfonic anhydride such as benzenesulfonic anhydride, p-bromobenzenesulfonic anhydride or methanesulfonic anhydride, in a base such as triethylamine. The products of the reaction are for example 2-deoxy-2,2-difluoro-D-ribofuranosyl-3,5-di-O-benzoyl-1-methanesulfonate and triethylammonium methanesulfonate.

The beta-anomer ribofuranosyl sulfonate and conjugate anion sulfonic acid are heated from about 50° C. to about 130° C. and more preferably to the reflux temperature of the solvent mixture.

Solvents suitable for use in the present anomerization process must be inert to the reaction conditions; preferred are acetonitrile, 1,2dichloroethane, 1,1,2-trichloroethane, chlorobenzene, bromobenzene, dichlorobromomethane, anisole, glyme, diglyme, methyl tertbutyl ether, tetrahydrofuran, dioxane, ethyl acetate, toluene, xylenes, pyridine, N-methylpyrrolidinone, N,N-dimethylformamide, 1,3-dimethyl-2-imidazolone, N,N-dimethylacetamide, and mixtures thereof; most preferred are anisole, toluene, glyme, acetonitrile, and mixture thereof.

In another embodiment of the present process, a catalyst selected from crown ethers or phase transfer catalyst is added to increase the solubility and nucloephilicity of metal salts used as the source of the conjugate anion of the sulfonic acid; preferred catalyst are selected from 18-Crown-6, 15-Crown-5, 12-Crown-4 and tris[2-(2-methoxyethoxy)ethyl]amine.

The present process is carried out under atmospheric conditions and preferably anhydrous conditions. The process is substantially complete in about 15 minutes to about 24 hours and more preferably in about 4 hours to about 16 hours.

In accordance with the present invention, the alpha-anomer enriched ribofuranosyl sulfonates of formula I may be prepared in an anomeric ratio of from about 2.3:1 to 3.0:1 alpha to beta and more preferably 2.5:1 alpha to beta.

The alpha-anomer enriched ribofuranosyl sulfonates of the present process may be isolated via the process described in Pending U.S. patent application Ser. No. 07/902,303, Attorney Docket X-7776, filed comtemporaneously herewith or by procedures known in the art such as chromotography or extraction.

The progress of the present process may be followed by using high pressure liquid chromatography (HPLC), thin layer chromatography (TLC) or nuclear magnetic resonance (NMR) spectroscopy and comparing the product obtained against a verified sample.

The following examples illustrate specific aspects of the present invention and are not intended to limit the scope thereof in any respect and should not be so construed.

EXAMPLE 1

Alpha-Anomer Enrichment of
2-Deoxy-2,2-Difluoro-D-Ribofuranosyl-3,5-Di-O-benzoyl-1-Methanesulfonate To an anomeric mixture of 2-deoxy-2,2-difluoro-D-ribofuranosyl-3,5-di-O-benzoyl-1-methanesulfonate (1.0 g, 97% beta-anomer) in acetonitrile (10 ml) was added N,N-dimethylbenzylammonium methanesulfonate (100 mg). The mixture was stirred and heated to reflux. HPLC analysis was used to determine the alpha to beta ratio of the titled product and provided the following:

| Time (hours) | alpha/beta |
| --- | --- |
| 0 | 1:32 |
| 16 | 1.0:1.4 |
| 24 | 2.3:1.0 |

EXAMPLE 2

Alpha-Anomer Enrichment of
2-Deoxy-2,2-Difluoro-D-Ribofuranosyl-3,5-Di-O-benzoyl-1-Methanesulfonate To an anomeric mixture of 2-deoxy-2,2-difluoro-D-ribofuranosyl-3,5-di-O-benzoyl-1-methanesulfonate (1.0 g, 50% beta-anomer) in acetonitrile (10 ml) was added N,N-dimethylbenzylammonium methanesulfonate (560 mg, 1.1 eq.). The mixture was stirred and heated to reflux. HPLC analysis was used to determine the alpha to beta ratio of the titled product and provided the following:

| Time (hours) | alpha/beta |
| --- | --- |
| 0 | 1.1:1.0 |
| 8 | 1.6:1.0 |
| 16 | 2.0:1.0 |
| 23 | 2.6:1.0 |

EXAMPLE 3

Alpha-Anomer Enrichment of
2-Deoxy-2,2-Difluoro-D-Ribofuranosyl-3,5-Di-O-benzoyl-1-Toluenesulfonate To 2-deoxy-2,2-difluoro-D-ribofuranosyl-3,5-di-O-benzoyl-1-toluenesulfonate (1.0 g, 100% beta-anomer) in acetonitrile (10 ml) was added tetraethylammonium p-toluenesulfonate (570 mg, 1.1 eq.). The mixture was stirred and heated to reflux. HPLC analysis was used to determine the alpha to beta ratio of the titled product and provided the following:

| Time (hours) | alpha/beta |
| --- | --- |
| 0 | 100% beta |
| 3 | 2.2:1.0 |
| 16 | 2.3:1.0 |

EXAMPLE 4

Alpha-Anomer Enrichment of
2-Deoxy-2,2-Difluoro-D-Ribofuranosyl-3,5-Di-O-benzoyl-1-Toluenesulfonate To 2-deoxy-2,2-difluoro-D-ribofuranosyl-3,5-di-O-benzoyl-1-toluenesulfonate (1.0 g, 100% beta-anomer) in glyme (10 ml) was added tetraethylammonium p-toluenesulfonate (570 mg, 1.1 eq.). The mixture was stirred and heated to reflux for 16 hours. HPLC analysis was used to determine the alpha to beta anomer ratio which was 2.3:1.

EXAMPLE 5

Alpha-Anomer Enrichment of
2-Deoxy-2,2-Difluoro-D-Ribofuranosyl-3,5-Di-O-benzoyl-1-Toluenesulfonate To 2-deoxy-2,2-difluoro-D-ribofuranosyl-3,5-di-O-benzoyl-1-toluenesulfonate (49 g, 100% beta-anomer) in toluene (500 ml) was added tetraethylammonium p-toluenesulfonate (11.2 g, 0.2 eq.). The mixture was stirred and heated to 100° C.–105° C. An HPLC analysis was used to determine the alpha to beta ratio of the product and provided the following:

| Time (hours) | alpha/beta |
| --- | --- |
| 0 | 100% beta |
| 4.5 | 2.0:1.0 |
| 6.5 | 2.3:1.0 |

EXAMPLE 6

Alpha-Anomer Enrichment of
2-Deoxy-2,2-Difluoro-D-Ribofuranosyl-3,5-Di-O-benzoyl-1-(p-Bromobenzene)sulfonate An anomeric mixture of 2-deoxy-2,2-difluoro-D-ribofuranosyl-3,5-di-O-benzoyl-1-(p-bromobenzene)sulfonate (11.9 g, 85% beta-anomer), in dichloromethane (75 ml), containing triethylammonium (p-bromobenzene)sulfonate was heated to reflux for 22 hours. A reversed phase HPLC analysis was used to determine the alpha to beta ratio of the titled product to be 3 to 1.

To isolate the alpha enriched sulfonate, the reaction mixture was poured over 100 ml of cold saturated aqueous potassium bisulfate solution. The organic layer was separated, washed with water, dried over anhydrous magnesium sulfate, and concentrated to provide a colorless oil which was chromatographed over silica gel using toluene as eluant to provide 11.8 grams or a 99 percent yield of the titled product in a 3:1 alpha to beta ratio.

Further product enrichment could be achieved by crystallizing out unwanted beta-sulfonate starting material using a mixture of ethyl acetate and isooctane. After filtering off the beta-anomer sulfonate, the filtrate was concentrated to constant weight to provided a 70% by weight recovery of alpha-bromobenzenesulfonate. Analysis by reversed phase HPLC indicated an increased alpha to beta ratio of 9:1. QE300 $^1$HNMR(CDCl$_3$). δ'=8.02(m, 4H, Ar), 7.62(m, 2H, Ar), 7.7−7.54(m, 4H, Ar), 7.46(m, 4H, Ar) 6.11(d, 1H, 1-H), 5.5−5.45 (dd, 1H, 3-H) 4 67–4.44(m, 3H, 4-H and 5-H).

EXAMPLE 7

Alpha-Anomer Enrichment of
2-Deoxy-2,2-Difluoro-D-Ribofuranosyl-3,5-Di-O-benzoyl-1-(p-Bromobenzene)sulfonate To 2-deoxy-2,2-difluoro-D-ribofuranosyl-3,5-di-O-benzoyl-1-(p-bromobenzene)sulfonate (60 mg, 100% beta-anomer), in acetonitrile (4 ml) was added the potassium salt of p-bromobenzenesulfonic acid (130 mg). The mixture was heated to reflux for 2 hours. Reversed phase HPLC indicated the anomerization to be approximately 10 percent complete. A catalyst (18-Crown-6)

was added and the mixture was heated to reflux for 20 hours. HPLC analysis was used to determine the alpha to beta ratio of the titled product to be 7:3.

EXAMPLE 8

Alpha-Anomer Enrichment of 2-Deoxy-2,2-Difluoro-D-Ribofuranosyl-3,5-Di-O-benzoyl-1-(p-Bromobenzene)sulfonate To 2-deoxy-2,2-difluoro-D-ribofuranosyl-3,5-di-O-benzoyl-1-(p-bromobenzene)sulfonate (600 mg, 100% beta-anomer), in acetonitrile (25 ml) was added the potassium salt of p-bromobenzenesulfonic acid (260 mg) and tris[2-(2-methoxyethoxy)ethyl]amine. The mixture was stirred and heated to reflux for 4.5 hours. Reversed phase HPLC analysis was used to determine that the anomerization was 40 percent complete. The reaction was refluxed for a total of 28 hours. The alpha to beta ratio of the titled product was determined by HPLC analysis to be 3:1.

In order to obtain pure alpha-anomer 2-deoxy-2,2-difluoro-D-ribofuranosyl-1-(p-bromobenzene)sulfonate, the reaction mixture in Example 8 was evaporated under reduced pressure. The residue was partitioned with ethyl acetate and cold aqueous 1 N HCl. The ethyl acetate layer was washed with additional aqueous HCl solution, dried over anhydrous magnesium sulfate, and concentrated to an oil. The oil was repeatedly chromatographed over silica gel using 5% tetrahydrofuran in isooctane for elution. After multiple small-scale chromatography, the appropriate fractions were pooled, dried over anhydrous magnesium sulfate and concentrated to provide a clear, colorless oil which was the desired 2-deoxy-2,2-difluoro-D-ribofuranosyl-1-α-(p-bromobenzene)sulfonate. HPLC analysis provided an alpha to beta ratio of 99:1.

EXAMPLE 9

Alpha-Anomer Enrichment of 2-Deoxy-2,2-Difluoro-D-Ribofuranosyl-3,5-Di-O-benzoyl-1-Toluenesulfonate To 2-deoxy-2,2-difluoro-D-ribofuranosyl-3,5-di-O-benzoate (1 g, 100% beta-anomer) was added p-toluenesulfonic anhydride (.94 g), toluene (10 ml) and triethylamine (0.37 ml). The mixture was stirred and heated to 95° C. Reversed phase HPLC analysis was used to determine whether the anomerization was complete. The alpha to beta ratio of the titled product was determined by HPLC analysis to be 2.4:1.

EXAMPLE 10

Alpha-Anomer Enrichment of 2-Deoxy-2,2-Difluoro-D-Ribofuranosyl-3,5-Di-O-benzoyl-1-Toluenesulfonate To 2-deoxy-2,2-difluoro-D-ribofuranosyl-3,5-di-O-benzoate (1 g, 100% beta-anomer) was added p-toluenesulfonic anhydride (0.94 g), anisole (10 ml) and triethylamine (0.37 ml). The mixture was stirred and heated to 95° C. Reversed phase HPLC analysis was used to determine whether the anomerization was complete. The alpha to beta ratio of the titled product was determined by HPLC analysis to be 2.35:1.

EXAMPLE 11

Alpha-Anomer Enrichment of 2-Deoxy-2,2-Difluoro-D-Ribofuranosyl-3,5-Di-O-benzoyl-1-Methanesulfonate To an anomeric mixture of 2-deoxy-2,2-difluoro-D-ribofuranosyl-3,5-di-O-benzoyl-1-methanesulfonate (29.1 g, 50% beta-anomer) in dichloromethane and n-propyl acetate was heated to 90° C. to remove the dichloromethane. The mixture was cooled to 50° C.–60° C. and a mixture of triethylamine (5.33 ml, 0.55 eq) and methanesulfonic acid (2.04 ml, 0.55 eq.) in n-propyl acetate (2 ml) was added. The resulting mixture was heated to 95° C.–97° C. and stirred. The mixture contained 23.2 g of 2-deoxy-2,2-difluoro-D-ribofuranosyl-3,5-di-O-benzoyl-1-methanesulfonate. HPLC analysis was used to determine the alpha to beta ratio of the titled product and provided the following:

| Time (hours) | alpha/beta |
|---|---|
| 4 | 3:1 |

EXAMPLE 12

Alpha-Anomer Enrichment of 2-Deoxy-2,2-Difluoro-D-Ribofuranosyl-3,5-Di-O-benzoyl-1-Methanesulfonate To an anomeric mixture of 2-deoxy-2,2-difluoro-D-ribofuranosyl-3,5-di-O-benzoyl-1-methanesulfonate (40.86 g, 50% beta-anomer) in dichloromethane and anisole was heated to 115° C. to provide an oil which was reconstituted with anisole. The mixture was cooled to 50° C.–60° C. and a mixture of triethylamine (14.95 ml, 1.1 eq) and methanesulfonic acid (5.72 ml, 1.1 eq.) in anisole (19 ml) was added. The resulting mixture was heated to 90° C. and stirred. The mixture contained 36.7 g of 2-deoxy-2,2-difluoro-D-ribofuranosyl-3,5-di-O-benzoyl-1methanesulfonate. HPLC analysis was used to determine the alpha to beta ratio of the titled product and provided the following:

| Time (hours) | alpha/beta |
|---|---|
| 5.5 | 3:1 |

The following Table illustrates various embodiments of the present process.

| Sulfonate | % β | Acid Source | Equiv. | Solvent | α:β Ratio | α Yield |
|---|---|---|---|---|---|---|
| OMs | 46 | A | 1.1 | Acetonitrile | 2.6:1 | 72% |
| OMs | 97 | A | 0.2 | Acetonitrile | 2.3:1 | 69% |
| OTs | 99 | B | 1.0 | Acetonitrile | 2.3:1 | 69% |
| OTs | 99 | B | 1.0 | Acetonitrile | 2.3:1 | 69% |
| OTs | 99 | B | 1.0 | Glyme | 2.5:1 | 71% |
| OTs | 99 | B | 1.0 | 1,2-dichloroethane | 2.4:1 | 70% |
| OTs | 99 | B | 1.0 | Glyme | 2.5:1 | 71% |
| OTs | 99 | B | 1.0 | Toluene | 2.3:1 | 69% |
| OTs | 99 | B | 1.0 | Toluene | 2.3:1 | 69% |
| OTs | 99 | B | 0.2 | Toluene | 2.3:1 | 69% |

(A) is N,N-dimethylbenzylammonium methanesulfonate and (B) is tetraethylammonium p-toluenesulfonate. OMs is 2-deoxy-2,2-difluoro-D-ribofuranosyl-3,5-di-O-benzoyl-1-methanesulfonate and OTs is 2-deoxy-2,2-difluoro-D-ribofuranosyl-3,5-di-O-benzoyl-1-toluenesulfonate.

The present invention has been described in detail, including the embodiments thereof. However, it will be appreciated that those skilled in the art, upon consideration of the present disclosure, may make modifications and/or improvements on this invention that fall within the scope and spirit of the inventions as set forth in the following claims.

What is claimed is:

1. A process for providing an alpha-anomer enriched ribofuranosyl sulfonate of the formula

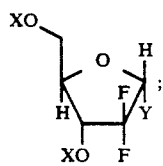
(I)

from a beta-anomer ribofuranosyl sulfonate of the formula

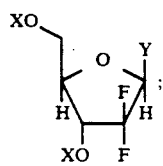
(II)

wherein Y is a sulfonate and each X is independently selected from hydroxy protecting groups; comprising treating a beta-anomer ribofuranosyl sulfonate of formula II with a source of a conjugate anion of a sulfonic acid, at elevated temperatures, in an inert solvent.

2. The process of claim 1 wherein Y is selected from the group consisting of methanesulfonyl, 2-chloro-1-ethanesulfonyl, toluenesulfonyl, p-nitrobenzenesulfonyl and p-bromobenzenesulfonyl.

3. The process of claim 2 wherein Y is methanesulfonyl.

4. The process of claim 2 wherein Y is toluenesulfonyl.

5. The process of claim 2 wherein Y is bromobenzenesulfonyl.

6. The process of claim 1 wherein the conjugate anion of a sulfonic acid is selected from the group consisting of alkali metal salts of methanesulfonic acid, ethanesulfonic acid, toluenesulfonic acid, 1-propanesulfonic acid, p-chlorobenzenesulfonic acid, p-bromobenzenesulfonic acid, benzenesulfonic acid and camphorsulfonic acid.

7. The process of claim 1 wherein the conjugate anion of a sulfonic acid is selected from the group consisting of amine salts of triethylammonium methanesulfonate, trimethylammonium methanesulfonate, N,N-dimethylbenzylammonium methanesulfonate, triethylammonium (p-chlorobenzene)sulfonate, triethylammonium (p-bromobenzene)sulfonate, pyridinium methanesulfonate, tetraethylammonium (p-toluene)sulfonate, pyridinium toluenesulfonate and pyridinium nitrobenzenesulfonate.

8. The process of claim 1 wherein the conjugate anion of a sulfonic acid is generated in-situ by reacting 2-deoxy-2,2-difluoro-D-ribofuranose with a sulfonic anhydride in a base such as triethyl amine.

9. The process of claim 1 wherein X is selected from the group consisting of mono-substituted benzoyl, di-substituted benzoyl and benzoyl.

10. The process of claim 9 wherein X is benzoyl.

11. The process of claim 1 wherein the solvent is selected from the group consisting of aromatic solvents, haloalkyl solvents, substituted aromatic solvents, and mixtures thereof.

12. The process of claim 11 wherein the solvent is selected from the group consisting of acetonitrile, dichloromethane, 1,2-dichloroethane, 1,1,2-trichloroethane, chlorobenzene, dichlorobromomethane, dibromochloromethane, tribromomethane, dibromomethane, anisole, glyme, diglyme, tetrahydrofuran, toluene, xylenes, pyridine, dimethylformamide, dimethylacetamide, and mixtures thereof.

13. The process of claim 12 wherein the solvent is selected from the group consisting of xylenes, toluene, glyme, anisole, acetonitrile and mixtures thereof.

14. The process of claim 13 wherein the solvent is selected from the group consisting of xylenes, anisole, acetonitrile, and mixtures thereof.

15. The process of claim 1 wherein the temperature is from about 50° C. to about 130° C.

16. The process of claim 15 wherein the temperature is the reflux temperature of the solvent mixture.

17. The process of claim 1 wherein the conjugate anion of a sulfonic acid is N,N-dimethylbenzylammonium methanesulfonate and Y is methanesulfonyl.

18. The process of claim 1 wherein the conjugate anion of a sulfonic acid is N,N-tetraethylammonium (p-toluene)sulfonate and Y is toluene sulfonate.

19. The process of claim 1 wherein the conjugate anion of a sulfonic acid is the potassium salt of (p-bromobenzene)sulfonic acid and Y is p-bromo benzenesulfonyl.

20. The process of claim 1 wherein the conjugate anion of a sulfonic acid is N,N-tetraethylammonium p-bromobenzenesulfonate and Y is p-bromobenzenesulfonyl.

21. The process of claim 1 wherein the source of the conjugate anion of a sulfonic acid is triethylammonium p-bromobenzenesulfonate and Y is p-bromobenzenesulfonyl.

22. The process of claim 6 further comprising adding a catalyst selected from phase transfer catalyst and crown ether catalyst.

* * * * *

UNITED STATES PATENT AND TRADEMARK OFFICE
CERTIFICATE OF CORRECTION

PATENT NO.    :   5,256,798

DATED         :   October 26, 1993

INVENTOR(S)   :   Ta-Sen Chou, et al.

It is certified that an error appears in the above-identified patent and that said Letters Patent is hereby corrected as shown below:

Column 2, line 66, delete "dichlo-,".

Column 2, line 67, delete "roethane,".

Column 3, line 38, delete "t-butoxc-", and insert therefor --t-butoxy- --.

Column 4, line 57, delete "Attorney Docket X-7776,".

Column 6, line 56, delete "4 67", and insert therefor --4.67--.

Column 3, line 6, delete "(4$\pi$ + 2) delocalized", and insert therefor --(4n +2) delocalized $\pi$--.

Column 3, line 7, delete "formula I", and insert therefor --formula II--.

Column 4, line 56, delete "comtempo-", and insert therefor --contempo- --.

Column 8, line 6, delete "eq)", and insert therefor --eq.)--.

Column 8, line 30, delete "eq)", and insert therefor --eq.)--.

UNITED STATES PATENT AND TRADEMARK OFFICE
CERTIFICATE OF CORRECTION

PATENT NO. : 5,250,361

DATED : October 5, 1993

INVENTOR(S) : Ide et al

It is certified that error appears in the above-identified patent and that said Letters Patent is hereby corrected as shown below:

Column 4, line 28, "exhibits"; should read --exhibit--.

Column 5, line 15, "glycidy"; should read --glycidyl--.

Column 15, line 15, "Mn = 3200)"; should read --Mn = 3200]--;
line 35, "Mn=3800)"; should read --Mn=3800]--;
line 51, "Mn = 3200)"; should read --Mn = 3200]--.

Column 16, line 9, "Mn = 3200)"; should read --Mn = 3200]--;
line 47, "Mn = 3200)"; should read --Mn = 3200]--.

Column 17, line 14, "Mn = 3200)"; should read --Mn = 3200]--.

Column 18, line 15, "Mn = 3200)"; should read --Mn = 3200]--.

Column 25, line 39, "Mn = 3200)"; should read --Mn = 3200]--.

Column 26, line 15, "Mn = 3200)"; should read --Mn = 3200]--.

Column 27, line 7, "Mn = 3200)"; should read --Mn = 3200]--;
line 61, "Mn = 3200)"; should read --Mn = 3200]--.

Column 28, line 48, "Mn = 3200)"; should read --Mn = 3200]--.

Column 31, line 14, "Mn = 3600)"; should read --Mn = 3600]--.

Column 32, line 21, "Mn = 3600)"; should read --Mn = 3600]--.

Column 33, line 22, "condensation"; should read --polycondensation--.

UNITED STATES PATENT AND TRADEMARK OFFICE
CERTIFICATE OF CORRECTION

PATENT NO. : 5,250,361

DATED : October 5, 1993

INVENTOR(S) : Ide et al

It is certified that error appears in the above-identified patent and that said Letters Patent is hereby corrected as shown below:

Column 35, line 9, "Mn = 3000)"; should read --Mn = 3000]--;
lines 58-59, "[weight ratio ... Mn = 3000)"; should read --(weight ratio ... Mn = 3000]--.

Column 36, line 30, "Mn = 3000)"; should read --Mn = 3000]--.

Column 37, line 14, "Mn = 3000)"; should read --Mn = 3000]--;
line 63, "Mn = 3000)"; should read --Mn = 3000]--.

Column 38, line 46, "Mn = 3000)"; should read --Mn = 3000]--.

Column 41, line 30, "4 5 $\mu$m"; should read --4.5 $\mu$m--.

Column 42, line 7, "Formation on of"; should read --Formation of--.

Column 47, line 26, "claim 7"; should read --claim 6--;
line 29, "claim 9"; should read --claim 7--.

Column 48, line 12, "n the range"; should read --in the range--.

Signed and Sealed this

Thirteenth Day of December, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,256,798

DATED : October 26, 1993

INVENTOR(S) : Ta-Sen Chou, et al

It is certified that error appears in the above-indentified patent and that said Letters Patent is hereby corrected as shown below:

Column 2, line 66, delete "dichlo-,".

Column 2, line 67, delete "roethane,".

Column 3, line 38, delete "t-butoxc-", and insert therefor --t-butoxy- --.

Column 4, line 57, delete "Attorney Docket X-7776,".

Column 6, line 56, delete "4 67", and insert therefor --4.67--.

Column 3, line 6, delete "(4$\pi$ + 2) delocalized", and insert therefor --(4n +2) delocalized $\pi$--.

Column 3, line 7, delete "formula I", and insert therefor --formula II--.

Column 4, line 56, delete "comtempo-", and insert therefor --contempo- --.

UNITED STATES PATENT AND TRADEMARK OFFICE
CERTIFICATE OF CORRECTION

PATENT NO. : 5,256,798

DATED : October 26, 1993

INVENTOR(S) : Ta-Sen Chou, et al

It is certified that error appears in the above-indentified patent and that said Letters Patent is hereby corrected as shown below:

Column 8, line 6, delete "eq)", and insert therefor --eq.)--.

Column 8, line 30, delete "eq)", and insert therefor --eq.)--.

This certificate supersedes Certificate of Correction issued December 13, 1994

Signed and Sealed this

Twenty-ninth Day of August, 1995

Attest:

BRUCE LEHMAN

*Attesting Officer*    *Commissioner of Patents and Trademarks*